(12) United States Patent
Catalano et al.

(10) Patent No.: US 7,970,549 B1
(45) Date of Patent: Jun. 28, 2011

(54) SYSTEM AND METHOD FOR HIGH-CONTENT ONCOLOGY ASSAY

(75) Inventors: Susan Catalano, Hayward, CA (US); John McLaughlin, Stanford, CA (US)

(73) Assignee: Rigel Pharmaceuticals Inc., South San Francisco, CA (US)

( * ) Notice: Subject to any disclaimer, the term of this patent is extended or adjusted under 35 U.S.C. 154(b) by 564 days.

(21) Appl. No.: 10/652,440

(22) Filed: Aug. 28, 2003

Related U.S. Application Data

(60) Provisional application No. 60/406,714, filed on Aug. 28, 2002.

(51) Int. Cl.
*G01N 33/48* (2006.01)
*G06G 7/48* (2006.01)
*C12Q 1/68* (2006.01)

(52) U.S. Cl. .................... 702/19; 435/6; 702/13
(58) Field of Classification Search ............ 422/50; 435/6, 7, 283.1; 702/19, 20, 22
See application file for complete search history.

(56) References Cited

U.S. PATENT DOCUMENTS

| 5,989,835 | A | 11/1999 | Dunlay et al. | |
| 6,759,206 | B1 * | 7/2004 | Rubin et al. | 435/7.2 |

FOREIGN PATENT DOCUMENTS

| WO | WO 01/31335 A2 | 5/2001 |
| WO | WO 01/31335 A3 | 5/2001 |
| WO | WO 01/92467 A2 | 12/2001 |
| WO | WO 02/00940 A2 | 1/2002 |

OTHER PUBLICATIONS

Chen et al. "Targeted disruption of the *Dictostelium myosin* essential light chain gene produces cells defective in cytokinesis and morphogenesis", Journal of Cell Science, (1995), vol. 108, pp. 3207-3218.*
Wong et al. "Forced Expression of a Dominant-Negative Chimeric Tropmyosin Causes Abnormal Motile Behavior During Cell Division", Cell Motility and the Cytoskeleton, (2000), vol. 45, pp. 121-132.*
Li et al. "Interphase Cell Cycle Dynamics of a Late Replicating, Heterochromatic Homogenity Staining Region: precise Choreography of Condensation/Decondensation and Nuclear Positioning" The Journal of Cell Biology (1998) vol. 140, pp. 975-989.*
Fay et al. "Quantitative Digital Analysis of Diffuse and Conetrated Nuclear Distrobutions of Nascent Transcripts, SC35 and Poly(A)" Experimental Cell Research (1997), vol. 23, pp. 27-37.*

* cited by examiner

*Primary Examiner* — Eric S DeJong
(74) *Attorney, Agent, or Firm* — James S. Keddie; Travis Young; Carol L. Francis

(57) ABSTRACT

The present invention provides an apparatus, system, method and computer program and computer program product for analyzing cellular samples. One embodiment of the apparatus and method provides a multiparameter assay that provides information with respect to cell proliferation, cell cycling and cell death. The multiparameter assay is particularly useful for assessing and screening candidate compounds for anti-cancer utility.

17 Claims, 13 Drawing Sheets

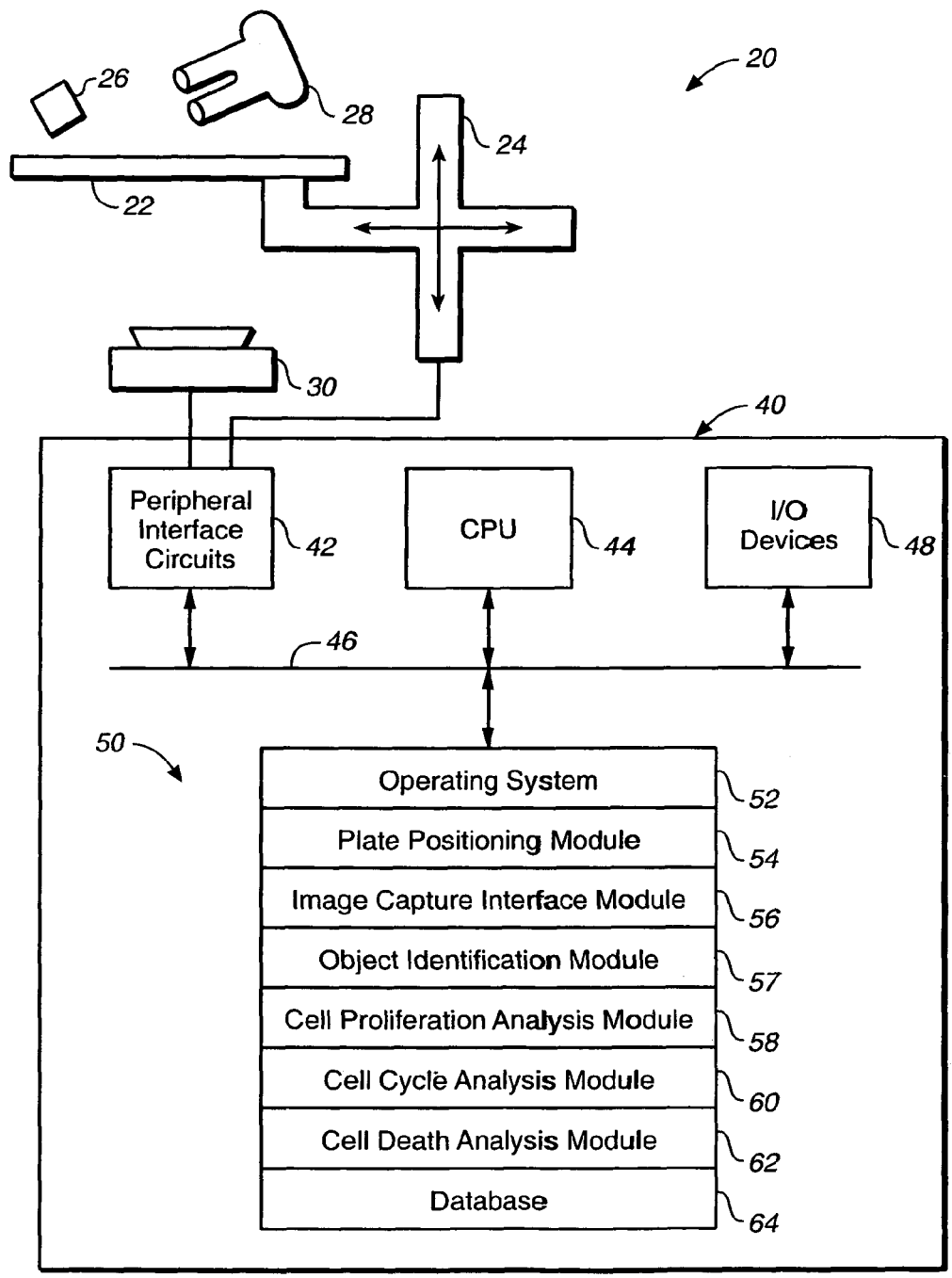
FIG._1

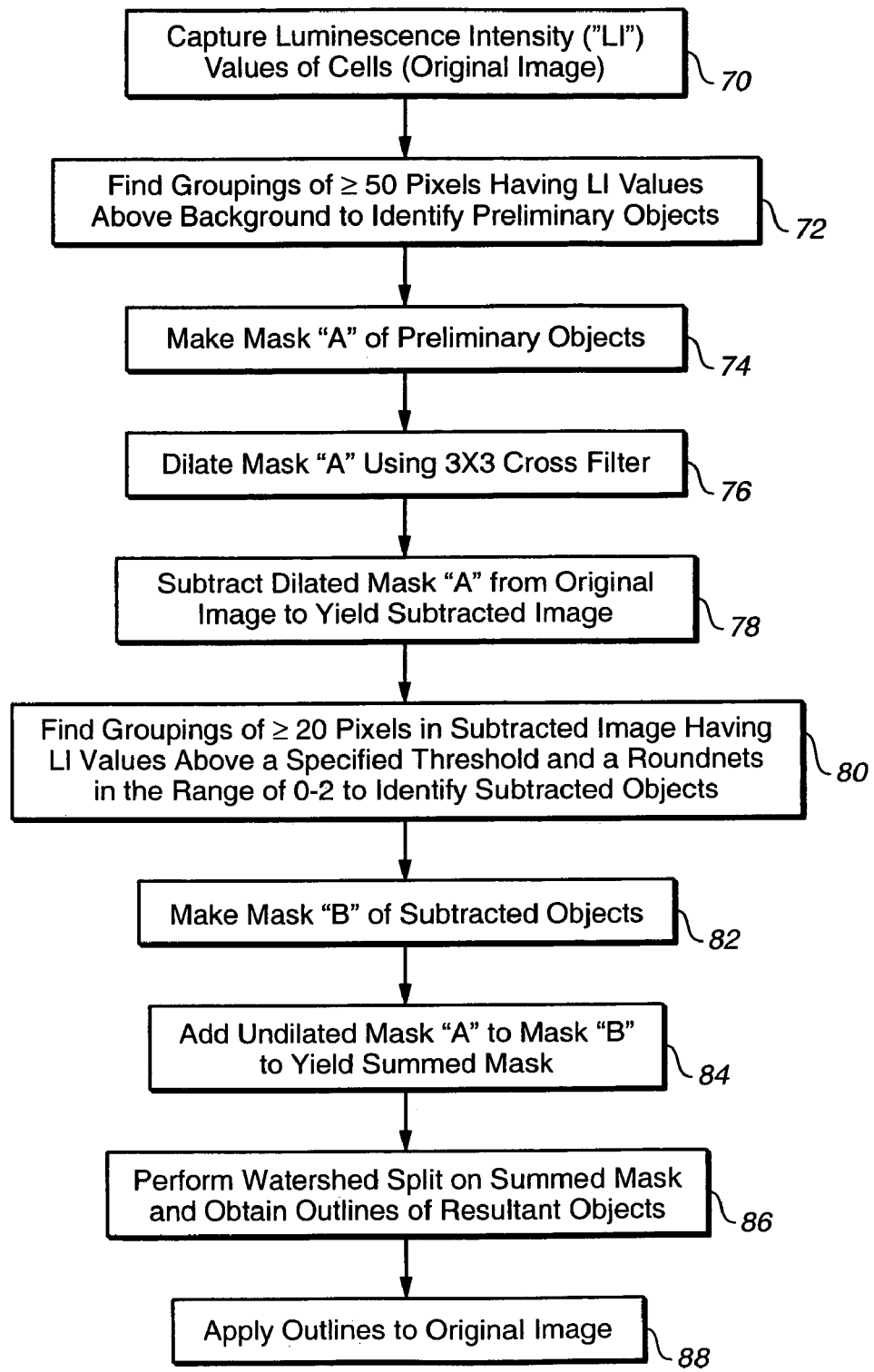
FIG._2

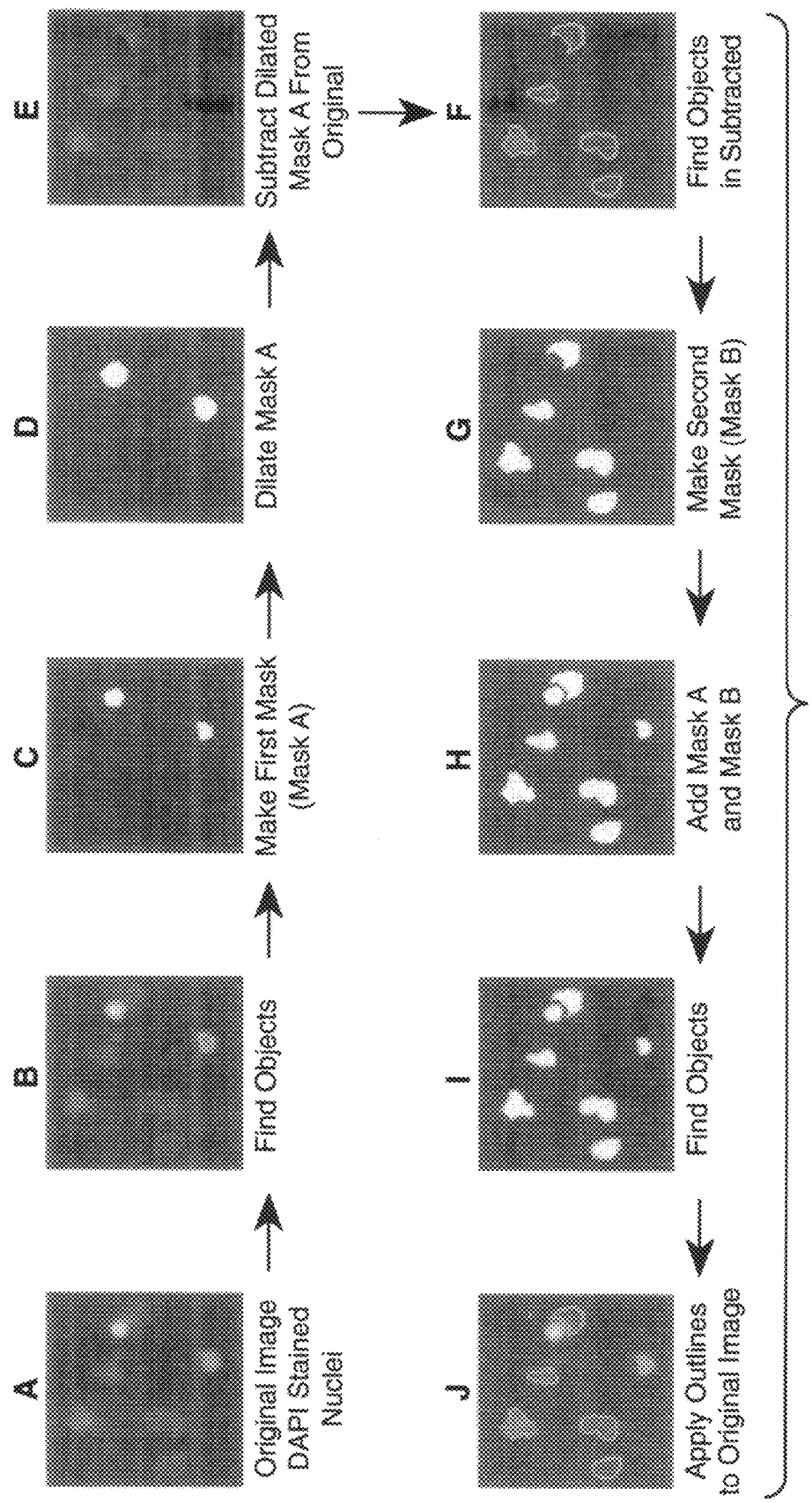
FIG._3

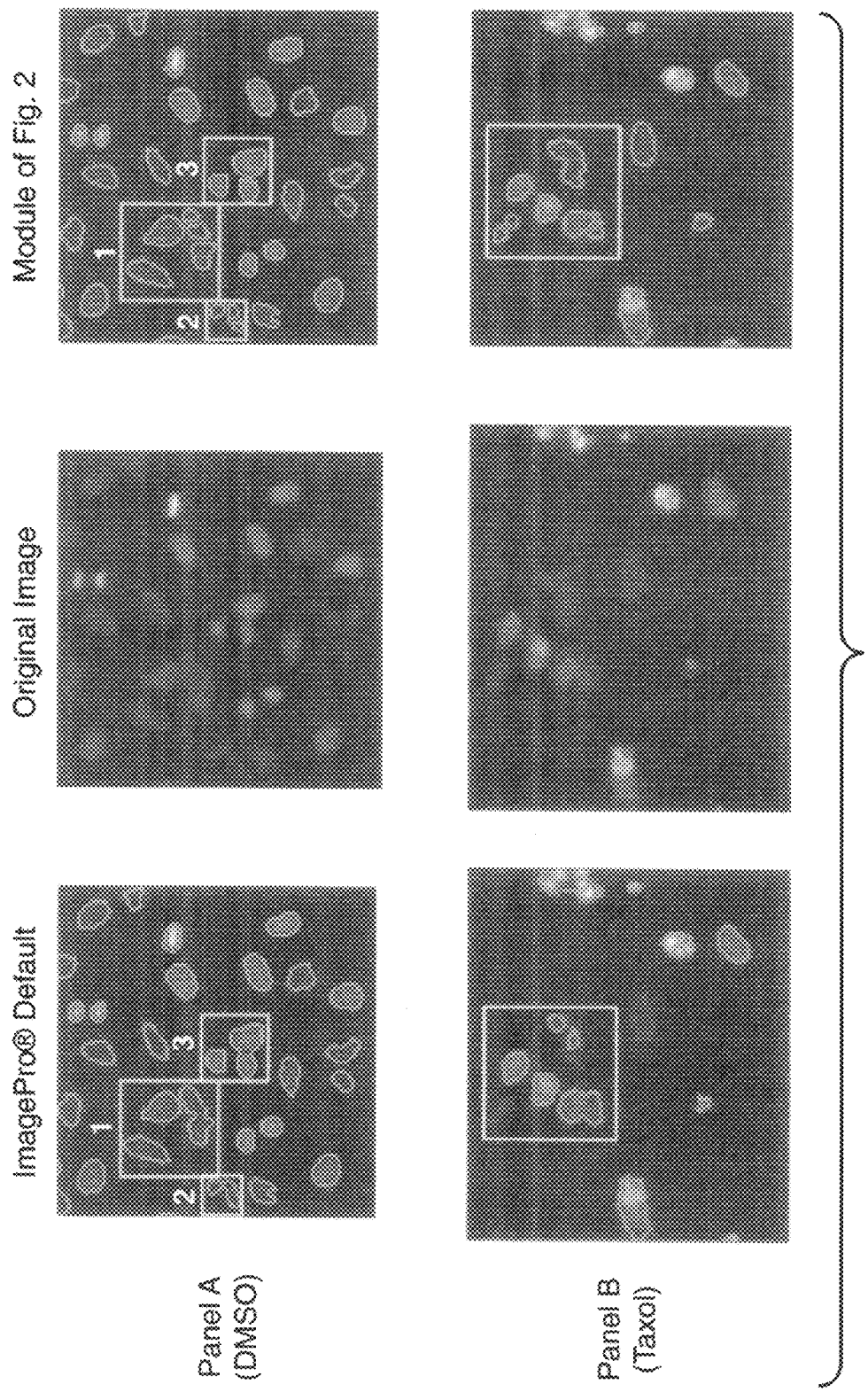
FIG._4A

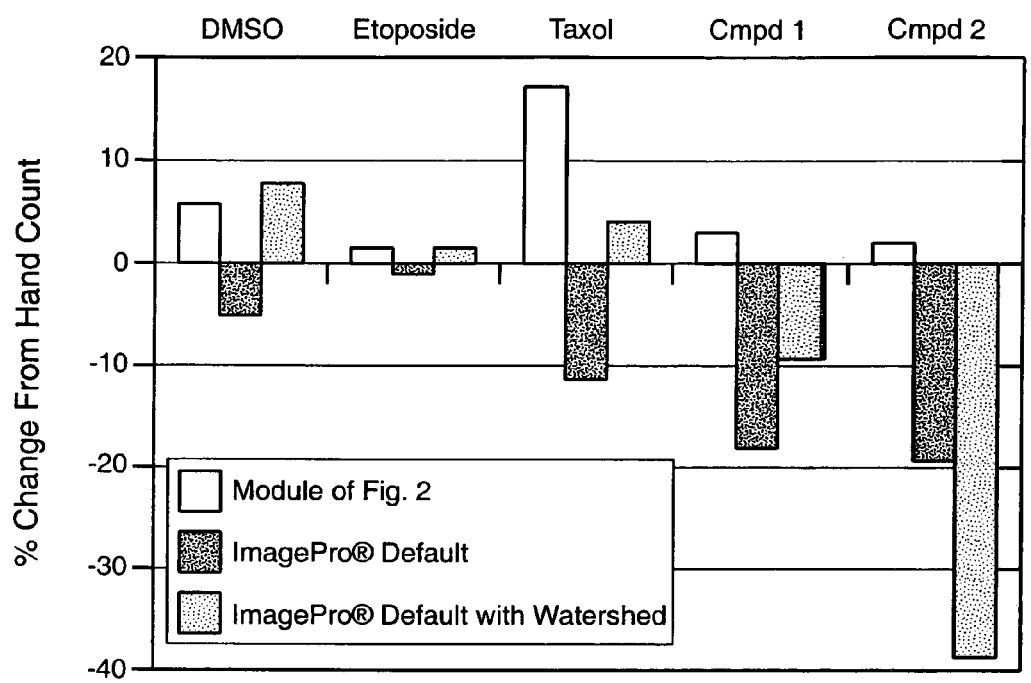
FIG._4B

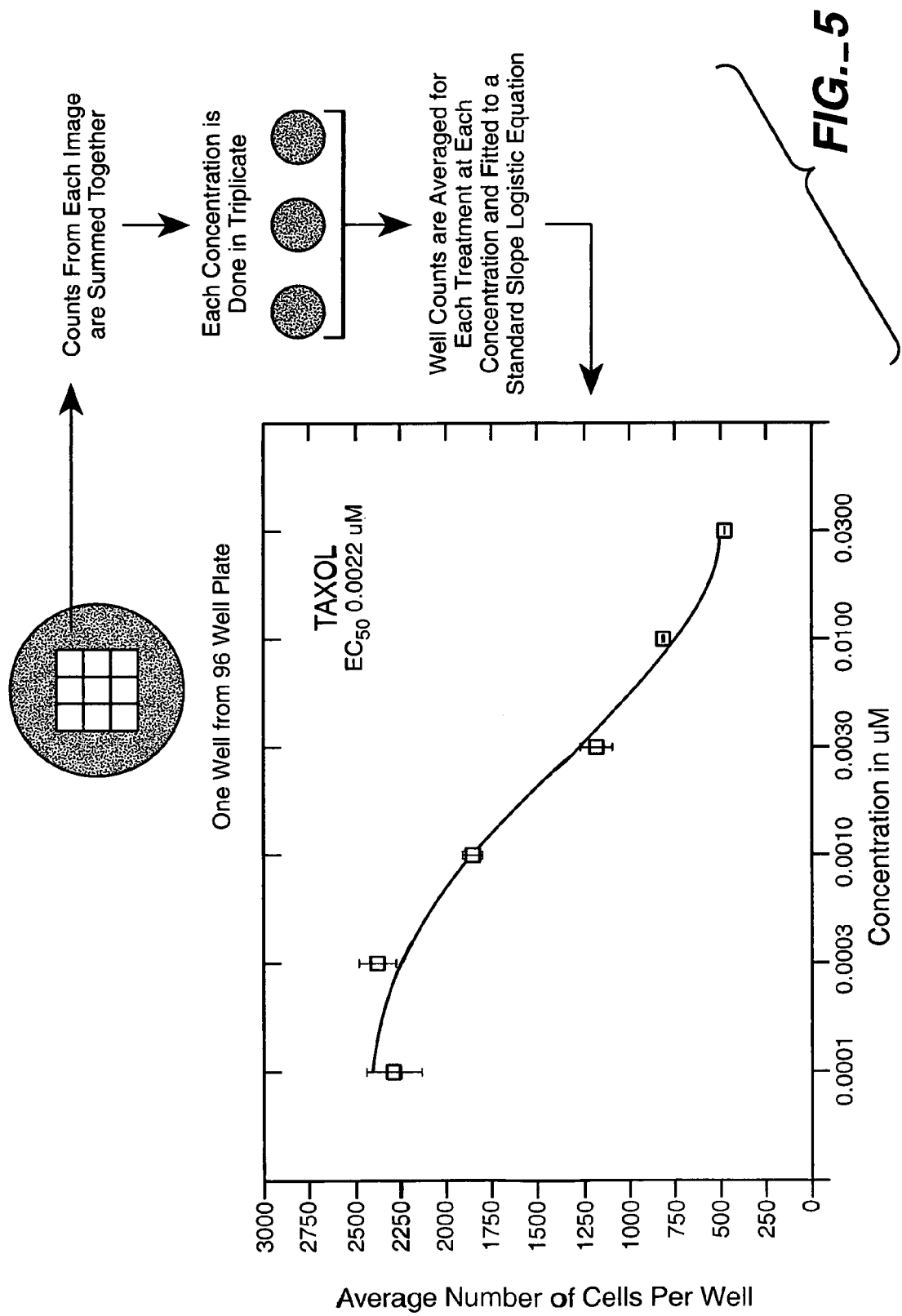
FIG._5

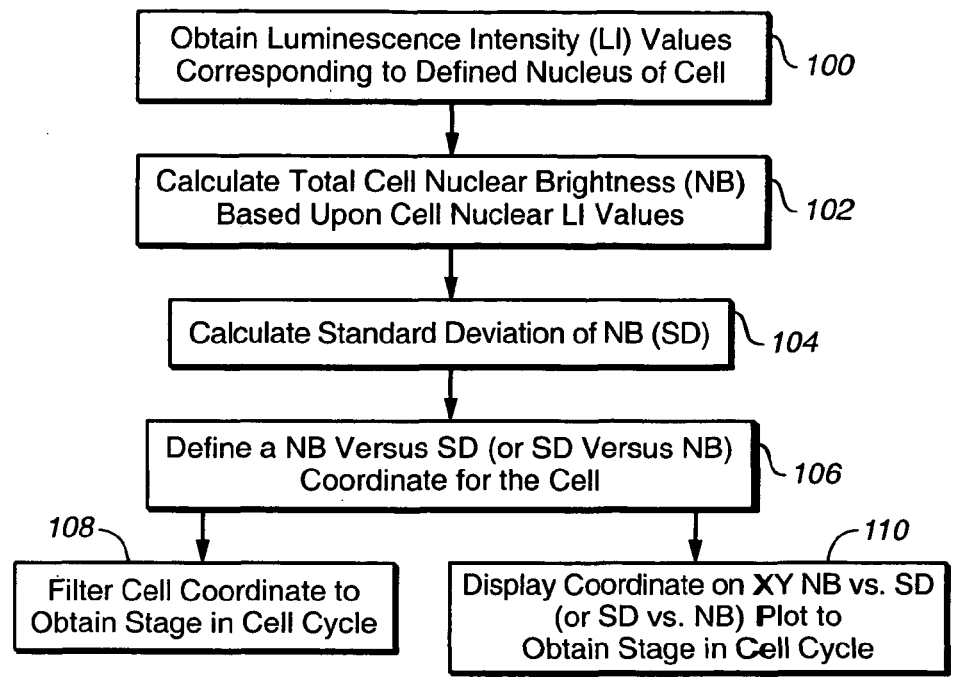
FIG._6A
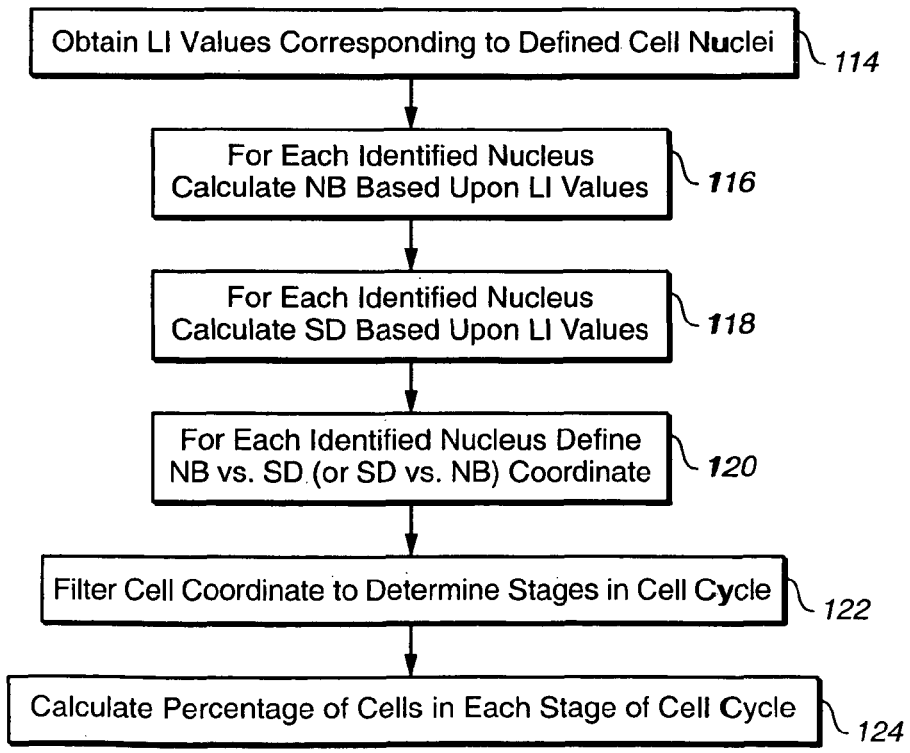
FIG._6B

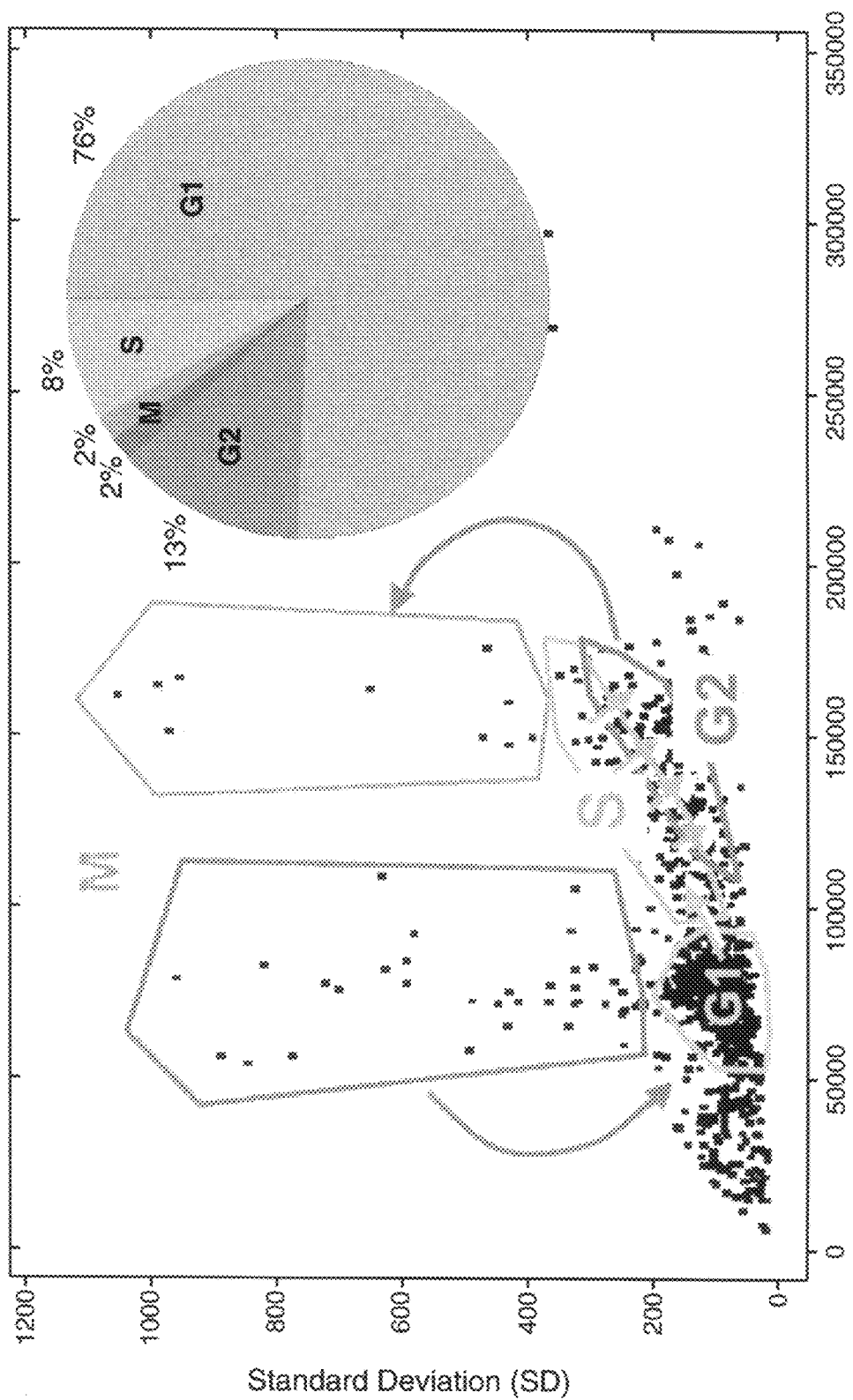
FIG._7

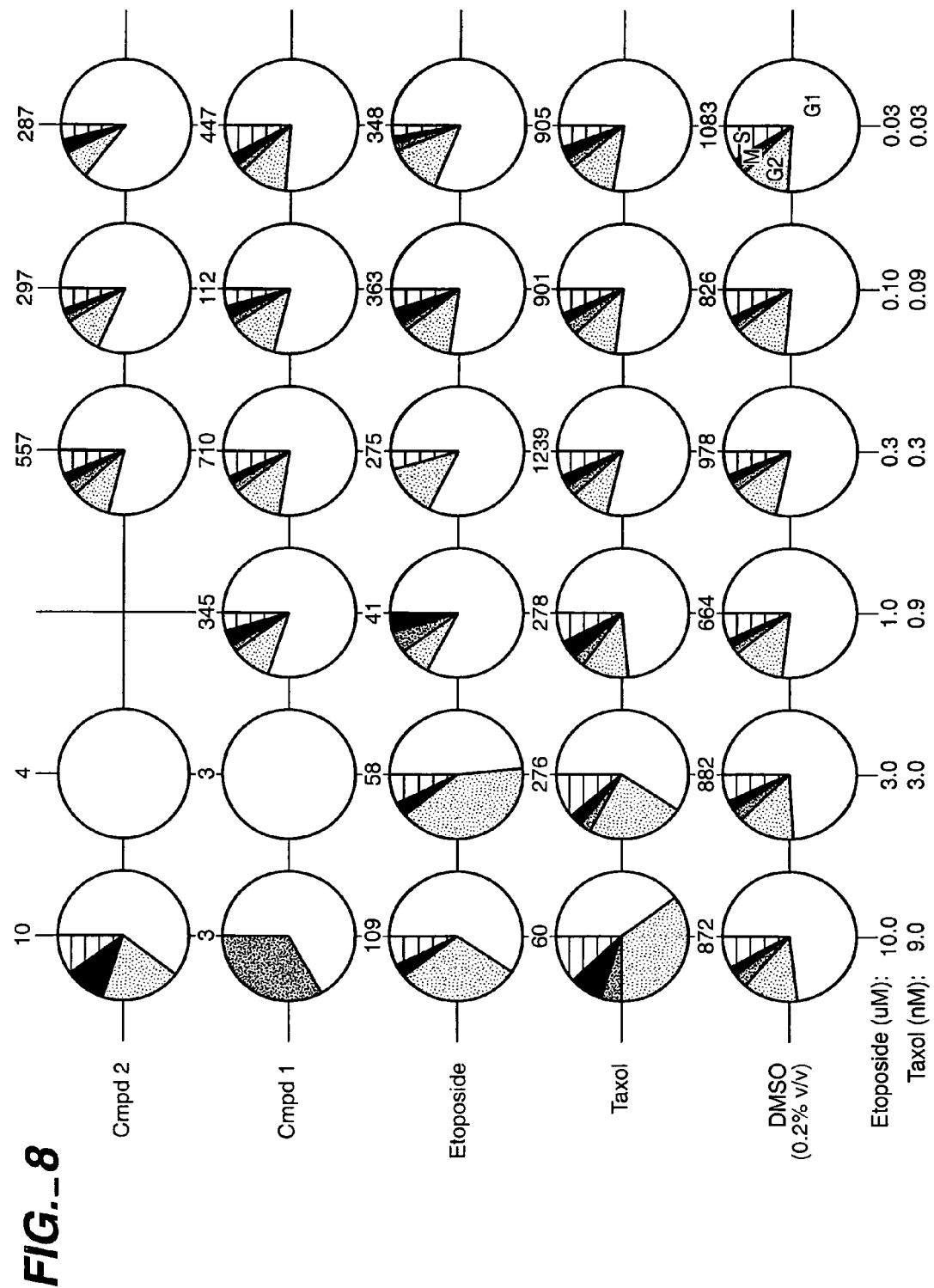
FIG._8

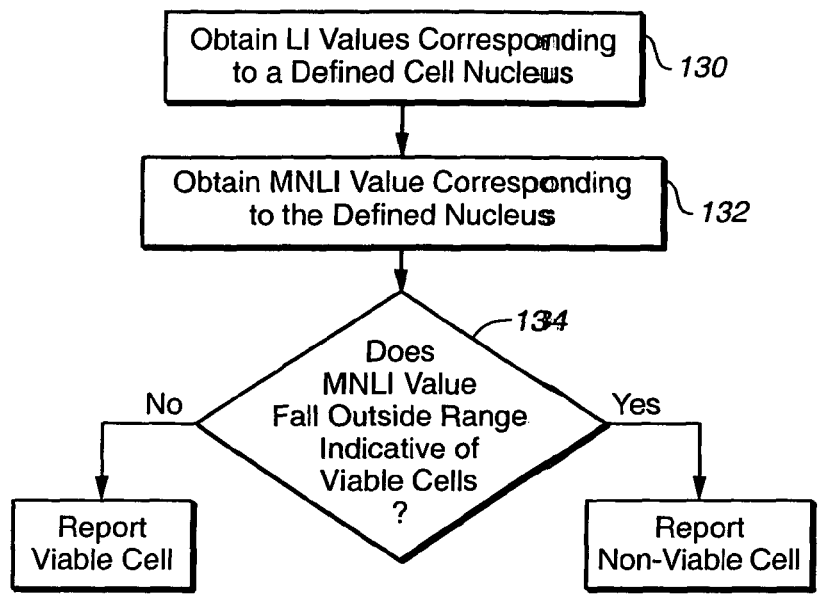
FIG._9A
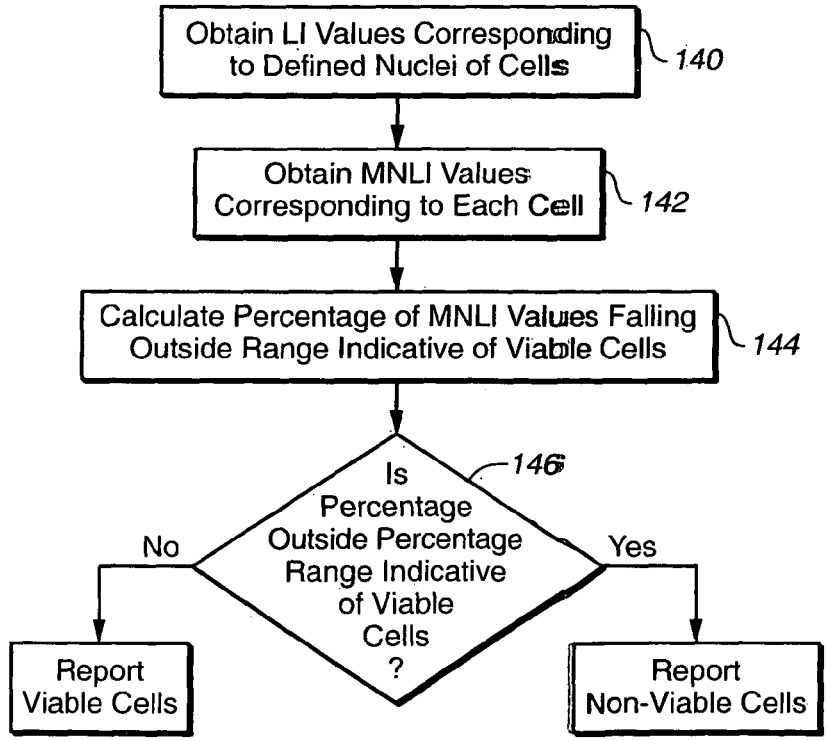
FIG._9B

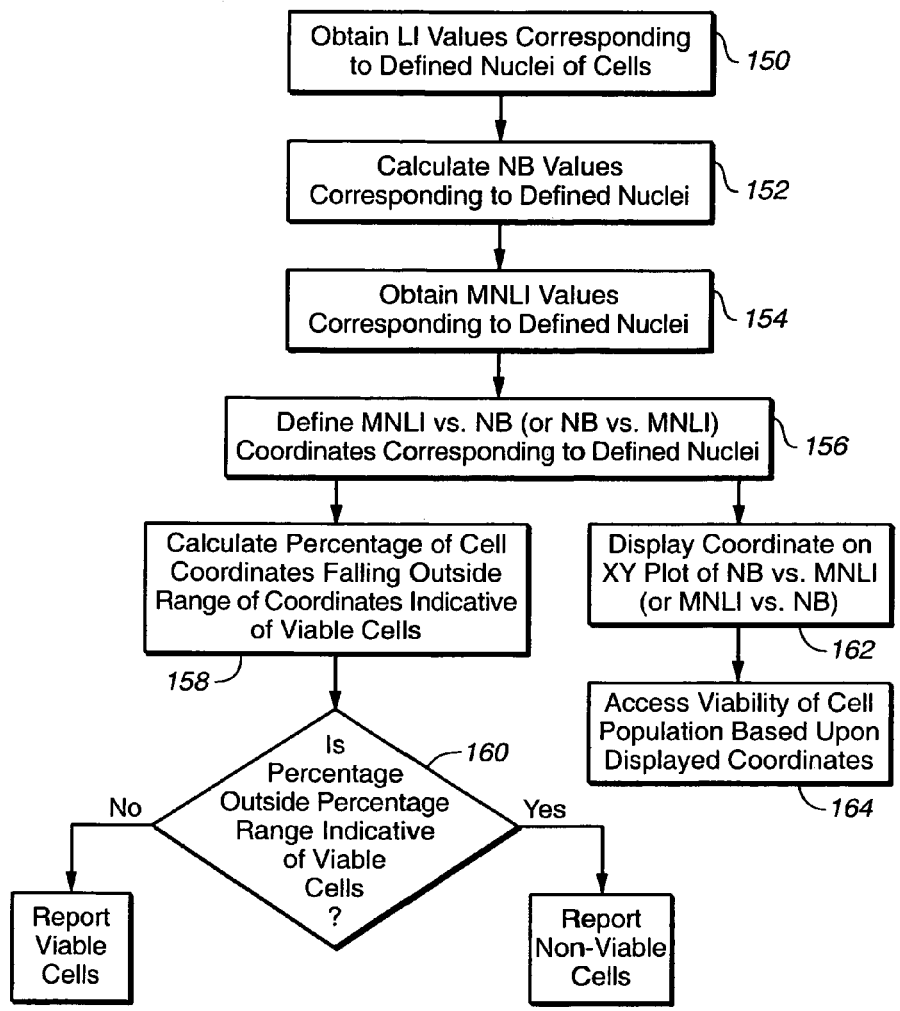
FIG._9C

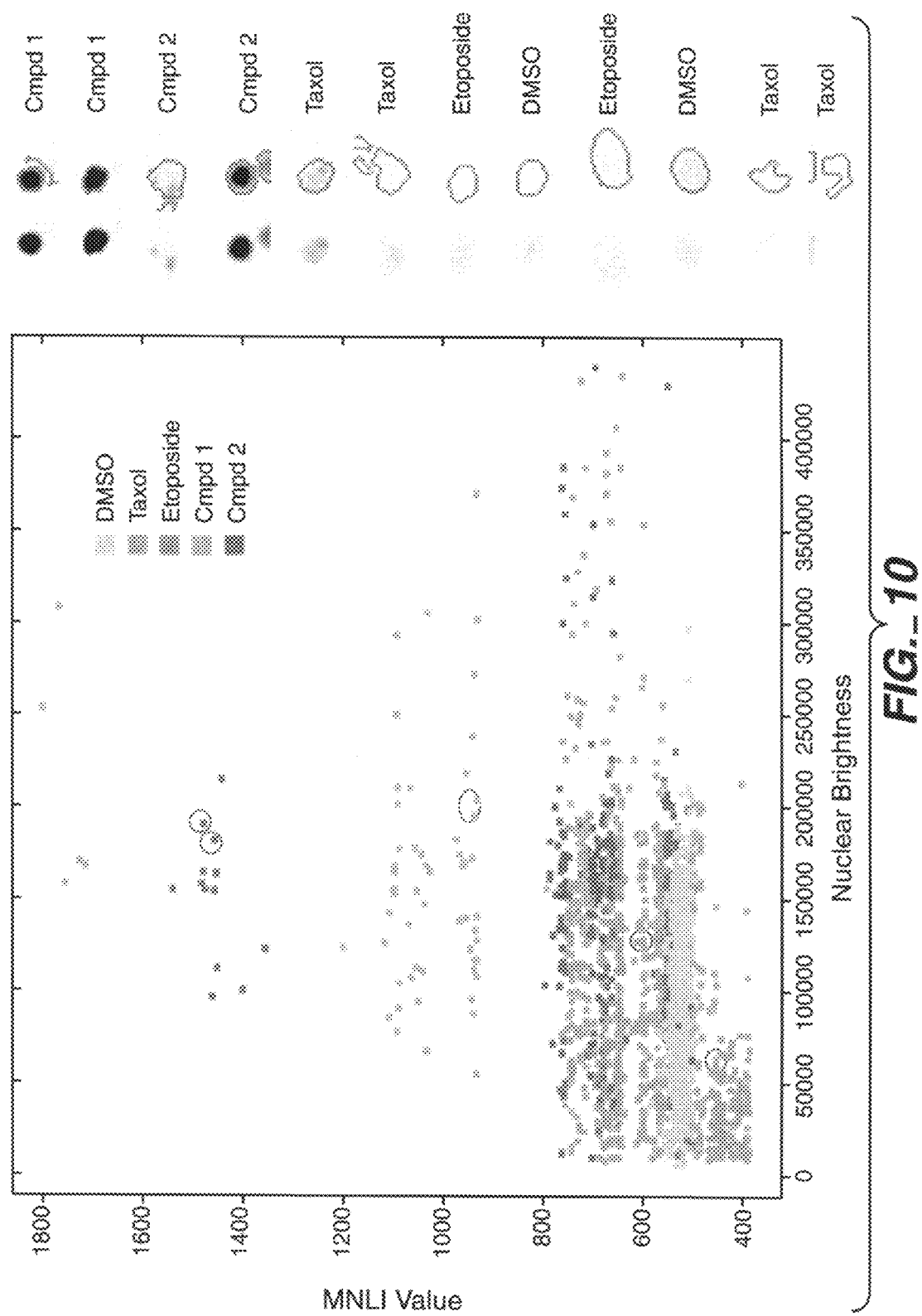
FIG._10

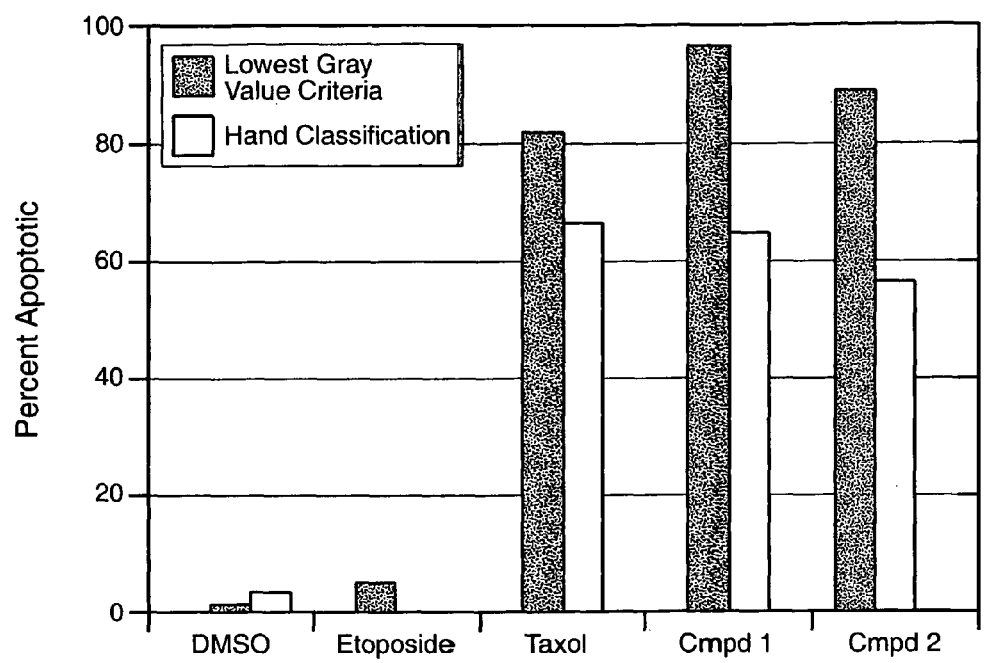
FIG._11

SYSTEM AND METHOD FOR HIGH-CONTENT ONCOLOGY ASSAY

RELATED APPLICATIONS

This application claims the benefit of priority under 35 U.S.C. 119(e) to U.S. Provisional Patent Application Ser. No. 60/406,714 filed 28 Aug. 2002 entitled SYSTEM AND METHOD FOR HIGH-CONTENT ONCOLOGY ASSAY, which application is hereby incorporated by reference.

FIELD OF THE INVENTION

The present invention relates to systems, apparatuses and methods useful for analyzing a sample of cells for proliferation, cell cycle phase, and/or death, and for screening candidate compounds for anti-proliferative effects on tumor and other types of cancer cells.

BACKGROUND OF THE INVENTION

Cancer is one of the most common causes of mortality in the U.S. Agents that can prevent the proliferation of tumor cells and/or induce their death are highly desirable in the fight against cancer. The process of tumor cell proliferation is extremely complex. Understanding tumor proliferation requires precise identification of multiple cell nuclei and detailed analysis of their phases in the cell cycle. Screening for agents able to halt proliferation and/or induce death of tumor and other cancer cells rely largely on biochemical and molecular biological approaches that are laborious and, in many instances, inadequate. Improved methods for screening cellular samples for proliferation, cell cycle phase, and/or death, as well as screening methods for identifying compounds capable of halting proliferation and/or inducing death, are needed.

SUMMARY OF THE INVENTION

In one aspect, the invention provides a system to analyze a cellular sample. An image capture device gathers luminescence intensity values corresponding to the nuclei of cells stained with a luminescent DNA-binding reporter molecule. A computer connected to the image capture device includes a peripheral interface circuit to receive the luminescence intensity values. A central processing unit is connected to the peripheral interface circuit. A memory is connected to the central processing unit. The memory operates under the control of the central processing unit. The memory includes an object identification module to identify and define nuclei of cells captured by the image capture device, and one or more of the following modules: a cell proliferation analysis module to count the defined nuclei, a cell cycle analysis module that provides information about cell cycling based upon the total nuclear brightness and standard deviation of nuclear brightness of the defined nuclei and/or a cell death analysis module that provides information about the viability of the cells based upon minimum luminescence intensity values corresponding to the defined nuclei.

In another aspect, the present invention provides a method of identifying objects in a sample based upon digital luminescence intensity values corresponding to the sample. According to the method, preliminary objects comprising groups of at least 50 pixels having luminescence intensity values above a first threshold (background) level are identified. An optional roundness parameter may be applied, the value of which will depend upon the overall morphology of the cells (e.g., round, oval, etc.) and will be apparent to those of skill in the art. A first mask of these preliminary objects is created, dilated and subtracted from the digital luminescence intensity values to yield a set of subtracted luminescence intensity values. From the subtracted luminescence intensity values, subtracted objects comprising groupings of at least 20 pixels having luminescence intensity values above a second threshold level, which may be the same or different from the first threshold level, and which have a specified roundness, which will depend upon the overall morphology of the cells are identified and a second mask of the subtracted objects is created. The undilated first mask is added to the second mask to yield a summed mask. A watershed split routine is applied to the summed mask, outlines of the resultant objects are obtained and the outlines are then applied to the original digital data, thereby defining objects in the original digital data. When the sample is a cellular sample stained with a luminescent DNA-binding reporter molecule, the defined objects correspond to nuclei of cells in the cellular sample.

In still another embodiment, the present invention provides a method of analyzing a cellular sample for proliferation. According to the method, nuclei corresponding to cells stained with a luminescent DNA-binding reporter molecule are identified and defined using the previously-described method of identifying objects. The defined nuclei are then counted. Determining the number of nuclei in the sample under a variety of conditions provides information about whether the cellular sample is proliferating. Thus, the method is particularly suited for identifying candidate compounds that inhibit cell proliferation. In one embodiment, the number of nuclei in a sample of cells treated with a candidate compound of interest as a function of time provides information about the ability of the test compound to inhibit proliferation of the cells. In another embodiment, the concentration of a candidate compound that inhibits 50% of cell proliferation (IC50 or ED50) can be determined by counting the number of nuclei of cellular samples of equal densities as a function of applied compound concentration.

In still another aspect, the present information provides a method of analyzing the cell cycle of a cell or the cell cycling of a population of cells. According to the method, nuclei of cells stained with a luminescent DNA-binding reporter molecule are identified as defined using the previously-described method of identifying objects. For each defined nucleus, a total nuclear brightness ("NB") versus standard deviation of total nuclear brightness ("SD") coordinate (or SD vs. NB coordinate) is obtained based upon the luminescence intensity values corresponding thereto. Information about the phase in the cell cycle of a particular cell, or about the cell cycling of a population of cells, is obtained based upon the coordinates. In one embodiment, a cell coordinate is filtered through a plurality of filters, each of which defines a set of coordinates corresponding to a particular phase in the cell cycle. Passage through or retention on a particular filter provides information about which phase in the cell cycle the cell is in. In an alternative embodiment, coordinates of a plurality of cells are filtered through the plurality of filters and the percentages of cells retained or passed through each filter calculated. The percentages provide information about the cycling of the cell population.

The method can be used in a variety of ways to identify candidate compounds that have an effect on cell cycling. As a specific example, the percentages of cells treated with a candidate compound of interest that are retained by each of the various filtered can be compared with the percentages retained by sister cultures of synchronous control cells. Differences in the observed percentages indicates the candidate compound has an effect on the cycling of the cells.

In still another aspect, the present invention provides a sensitive method of analyzing a cell for death, whether due to necrosis or apoptosis. According to the method, the minimum nuclear luminescence intensity ("MNLI") value corresponding to the nucleus of a cell that has been stained with a luminescent DNA-binding reporter molecule is determined. The MNLI value is then assessed to determine whether it falls outside a range of MNLI values indicative of viable cells. The range of MNLI values may be a predefined range of values or may be based upon the MNLI values corresponding to healthy, viable cells. The method may be used to analyze necrosis or apoptosis in a variety of contexts, and is particularly useful for analyzing necrosis or apoptosis in cells that have been exposed to, or contacted with, a candidate compound in order to identify compounds capable of inducing cell death.

In another aspect, the present invention provides a high-content assay that furnishes information on cell proliferation, cell death and cell cycle regulation. According to the method, luminescence intensity values corresponding to nuclei of one or more cells in a cellular sample are obtained. Information about cell proliferation, cell death and cell cycle regulation are then calculated from these values, as previously described.

The high-content assay may be used to analyze cellular samples in a variety of contexts, and is particularly useful for analyzing cells that have been exposed to, or contacted with, a candidate compound of interest to assess the effect(s) of the candidate compound on the cells. For example, the candidate compound may be assessed to determine whether it inhibits cell proliferation, arrests the cell cycle and/or induces cell death. Quite significantly, owing to the high information content provided by the assay, the high-content assay of the invention can be used not only to identify compounds that have potential anti-cancer activity, but to determine the mechanism by which the compounds exert their anti-cancer activity. The high-content assay of the invention therefore finds particular utility in screening libraries of candidate compounds to identify those library members that are anti-proliferative, that arrest cell cycle and/or that induce cell death, whether by necrosis or apoptosis. The ability of the high-content assay of the invention to distinguish between the mechanisms provides significant time and cost savings. Thus, information that is typically unavailable until late-phase secondary screens have been performed is now obtainable at the early initial screening phase.

The invention also provides computer program, computer program product, and computer code and/or computer memory to direct a computer to function in a specified manner. In one embodiment, executable instructions perform functions and/or processing algorithms that in conjunction with a computing machine identify or define nuclei of cells stained with a fluorescent DNA-binding reporter molecule based upon luminescence intensity values of the stained cells. Additional executable instructions perform tasks on collected data to provide information about cell proliferation, cell cycle regulation and/or cell death. In one embodiment, information about cell cycle regulation is provided by executing certain executable instructions in the processor and memory of the computer that calculate a total nuclear brightness versus standard deviation of nuclear brightness coordinate for each defined nucleus in the region. Additional executable instructions instruct the computer to compute a histogram of the coordinates. The histogram can be analyzed with additional executable instructions to assign each coordinate to a phase in the cell cycle, and/or the histogram can be output to a display device, which may be a printer, a video display or other display device, for visual analysis. Information about cell proliferation is provided by executing other executable instructions in the processor and memory (or CPU) of the computer that define and count the number of nuclei within the region. Information about cell death is provided by executable instructions that calculate MNLI values of the defined nuclei based upon the nuclear luminescence intensity values. Additional executable instructions assess whether the MNLI value falls outside a range of MNLI values indicative of viable cells.

BRIEF DESCRIPTION OF THE DRAWINGS

FIG. 1 provides a schematic representation of an apparatus of the invention;

FIG. 2 provides a schematic representation of one method of identifying nuclei according to the invention;

FIG. 3 provides images illustrating the method of FIG. 2;

FIG. 4A provides images illustrating the greater accuracy in defining nuclei achieved with the object identification module of FIG. 2 as compared with conventional object identification routines;

FIG. 4B provides a bar graph comparing the accuracy of three different nuclei identification routines with nuclei identified by visual inspection;

FIG. 5 provides a schematic demonstrating the use of the cell proliferation assay of the invention to measure IC50s or EC50s of cell proliferation;

FIGS. 6A-6B provide schematic representations of exemplary embodiments of the cell cycle assay of the invention;

FIG. 7 provides a graph of cell cycle data produced by the cell cycle assay of the invention;

FIG. 8 provides cell cycle data for cells treated with representative test compounds obtained with the cell cycle assay of the invention demonstrating the utility of the assay in screening methods to identify candidate compounds that affect cycling of cells;

FIGS. 9A-9C provide schematic representations of exemplary embodiments of the cell death assay of the invention;

FIG. 10 provides a graph showing the ability of the cell death assay of the invention to identify and distinguish compounds that induce cell death (taxol) from compounds that do not (DMSO, etoposide); and FIG. 11 provides a bar graph illustrating the accuracy of the cell death assay of the invention.

DETAILED DESCRIPTION OF THE PREFERRED EMBODIMENTS

FIG. 1 illustrates a system 20 configured in accordance with an embodiment of the invention. The system 20 includes a sample plate 22 for holding a cellular sample to be analyzed in accordance with the invention. The sample plate may be any type of sample plate commonly employed in the art for analyzing cellular samples. In one embodiment, the sample plate is a multiwell plate, such as a 96-well plate. The cells are typically adhered to the bottoms of the wells of the plate, preferably in a layer a single cell deep, using any of a variety of well-known techniques for adhering, attaching or fixing cells to cell sample plates. The cells are stained with a luminescent reporter molecule so that they, or their nuclei, can be visualized, as will be described in more detail, below. As a specific example, the cells are adherent cells that are cultured as a confluent or sub-confluent layer on the bottoms of the wells of the sample plate using standard techniques. Preferably, the position of the sample plate 22 is controlled by a plate position controller 24, which provides position control along an x-axis, y-axis, and z-axis. A light source 26 illuminates the sample plate 22. Depending upon the reporter molecule used to stain the cells, the light source 26 may cause the cells to emit light. A microscope 28 may be used to observe the sample. An image capture device 30 is focused on the sample plate 22. The image capture device is capable of receiving and preferably digitizing luminescence intensity values from the sample. In one embodiment of the invention, the image capture device 30 is a digital camera.

The image capture device 30 and the plate position controller 24 preferably operate under the control of a computer 40. The computer 40 includes peripheral interface circuits 42, which are connected to the plate position controller 24 and the image capture device 30. A central processing unit 44 is connected to the peripheral interface circuits 42 via a bus 46. Input/output devices 48 are also connected to the system bus 46. By way of example, the input/output devices 48 may include a keyboard, mouse, joystick, video monitor, printer, and the like.

A memory 50 is also connected to the system bus 46. The memory 50 stores a set of executable programs that are used to process the signals received by the peripheral interface circuits. The memory 50 stores an operating system 52 and a plate-positioning module 54. The plate-positioning module 54 is used to control the plate position controller 24. The memory also stores an image capture interface module 56, which is used to control the image capture device 30. In addition, the image capture interface module 56 may perform standard image processing tasks.

The components of the system 20 discussed up to this point are known in the art. U.S. Pat. No. 5,989,835, which is incorporated by reference, describes components of this type. The invention is directed toward the remaining methods, algorithms, computer programs, computer program products, and executable programs and instructions in memory 50 as well as computers and computing machines implementing and executing such methods, algorithms, computer programs, and instructions. These programs and instructions perform image-processing tasks in accordance with the invention.

In one embodiment of the invention, an object identification module 57 is stored in memory 50, typically including storage of a set of executable computer program instructions. The object identification module 57 includes executable code to identify objects, such as cell nuclei, from luminescence intensity ("LI") values secured by image capture device 30.

The memory 50 may also store a cell proliferation analysis module 58. The cell proliferation analysis module 58 includes executable code to count the objects, such as the cell nuclei, identified by the object identification module 57. The number of nuclei corresponds to the number of cells in the captured region of the sample.

The memory 50 may also store a cell cycle analysis module 60. The cell cycle analysis module 60 includes executable code to calculate total nuclear brightness ("NB") and standard deviation of nuclear brightness ("SD") values from LI values corresponding to nuclei secured by image capture device 30. Based upon these values, the cell cycle analysis module 60 then provides information about the cycle phases of the captured cells.

The memory 50 may also store a cell death analysis module 62. The cell death analysis module 62 includes executable code to determine the minimum nuclear luminescence intensity ("MNLI") value corresponding to one or more nuclei captured by the image capture device 30. Based upon these MNLI values, the cell death analysis module 62 provides information about the viability the captured cells.

The operation of these various modules is described in more detail, below.

The Object Identification Module

FIG. 2 illustrates one embodiment of processing steps associated with the operation of object identification module 57. The first processing step of FIG. 2 is to obtain luminescence intensity values of cells captured by image capture device 30 (block 70). A cell sample is placed on sample plate 22. The cells are stained with a luminescent DNA-binding reporter molecule, such as a fluorescent DNA-binding dye. Virtually any luminescent DNA-binding dye may be used, including fluorescent minor groove binding dyes such as indoles, imidazoles, bisbenzimides (e.g., Hoechst 33258, Hoechst 33342 and Hoechst 34580) 4',6-diamidino-2-phenylindole (DAPI) and fluorescent intercalating dyes such as phenanthridiniums (e.g., ethidium bromide, propidium iodide (PI), hexidium iodide, dihydroethidium, ethidium homodimers, etc) and acridines (e.g., acridine orange, acridine homodimer, 9-amino-6-chloro-2-methoxyacridine (ACMA)). Additional luminescent DNA-binding dyes that may be used are well-known and include, for example, the myriad dyes available from Molecular Probes, Inc. Preferably, the dye will either not bind RNA or luminesce differentially when bound to RNA (or single-stranded DNA) such that the nuclei of nucleated cells can be visualized. Of course, skilled artisans will appreciate that if the module is used to identify cells per se, or other components or organelles of cells, other suitable dyes may be used, as are well-known in the art.

Typically, the cells are stained with an amount of reporter molecule that binds to DNA in a linear range. Useful concentration ranges for providing linear DNA binding for specific dyes or reporter molecules are those commonly employed in FACS experiments, and are well-known in the art. For DAPI, it has been found that staining cells with a final DAPI concentration of about 5 ng/mL yields good results.

Light source 26 illuminates the cell sample. Depending upon the nature of the DNA-binding dye used, the illumination wavelength is selected so as to cause the dye to luminesce. For example, when the cells are stained with a fluorescent dye, an illumination wavelength is selected that causes the dye to fluoresce. Excitation wavelengths suitable for particular dyes are well-known in the art. The image capture device 30 subsequently obtains luminescent intensity values produced by the illuminated cells. For nucleated cells, the luminescent intensity values will correspond to the nuclei of the cells. Typically, the luminescence intensity values are associated with individual pixels. If a plurality of nuclei are captured by image capture device 30, luminescence intensity values corresponding to individual nuclei can be obtained and correlated with their respective nuclei.

The cell nuclei are identified from the luminescence intensity ("LI") values (also referred to herein as pixel gray values) as outlined in FIG. 2 and illustrated in FIG. 3. Referring to FIG. 3, image A shows a digital image corresponding to a DAPI-stained cellular sample captured by the image capture device. This image A may be either an image of the raw LI values captured by the image capture device or, alternatively, the image A may be an image that has been processed, for example to remove background luminescence using standard techniques. In this image A (or digital data corresponding thereto), pixels having a gray value that exceeds a first threshold (background) value are identified, and may be optionally designated as "on." Pixels having a gray value below this first threshold value may be turned "off." Groupings or clusters of 50 or more pixels that have gray values above the first threshold level, and which optionally have a specified roundness parameter (described in more detail, below), are identified as preliminary objects (defined in block 72 of FIG. 2 and illustrated in image B of FIG. 3).

The first threshold value will depend upon such parameters as background luminescence, the sensitivity of the dye used, etc., and will be apparent to those of skill in the art. By way of example, the threshold value may be set at a specific interval above measured background luminescence, either by the user or by the object identification module. If set by the module, the threshold value may be determined using standard routines for distinguishing signals from background noise. As a specific example, the threshold value may be determined using the signal to noise (S/N) routine employed by the ImagePro® software package supplied with an ArrayScan II® (Cellomics, Inc.) instrument. Alternatively, the first threshold level may be selected by the user from a set of predetermined values corresponding to particular reporter molecules.

A first mask ("mask A") is made from the preliminary objects (clusters of "on" pixels), as represented in block 74 of FIG. 2 and illustrated in image C of FIG. 3. In this image C, all pixels that correspond to a preliminary object are turned "on" and all pixels that do not correspond to a preliminary object are turned "off." The mask is dilated using standard dilation algorithms. As a specific example, the mask may be dilated for two passes using a 3×3 cross filter, as represented in block 76 of FIG. 2 and illustrated in image D of FIG. 3. The dilated mask A is subtracted from the original image (or digital data corresponding thereto) as represented in block 78 of FIG. 2 to yield a subtracted image as illustrated in image E of FIG. 3. Groupings or clusters of 20 or more pixels having gray values that exceed a second threshold value and that have a specified roundness parameter are identified in this subtracted image. This is the function described in block 80 of FIG. 2 and illustrated in image F of FIG. 3.

The second threshold value may be the same as the first threshold value, or it may be different. If different, it may be determined in the same manner as the first threshold value based upon the subtracted image (or digital data corresponding thereto).

The value of the roundness parameter applied (as well as the previously described optional roundness parameter) will depend upon the overall morphology of the cells (e.g., circular, oval, rodlike, etc.), and will be apparent to those of skill in the art. For circular and oval cells, such as most tumor cell lines except for HeLa cells, which are shaped like a horseshoe, a roundness parameter in the range of 0-2 yields good results. For HeLa cells, a roundness parameter of greater than 2 may be applied. Roundness parameters suitable for cells having other overall morphologies will be apparent to those of skill in the art.

In image F, the newly identified objects are defined with boundary lines. A second mask (mask "B") is made of such newly defined objects, as represented in block 82 of FIG. 2 and illustrated in image G of FIG. 3. To make mask B, pixels within the newly defined objects are turned "on" and all others are turned "off," as illustrated in image G. Undilated mask A and mask B are then added to create a third, summed mask, as represented in block 84 of FIG. 2 and illustrated in image H of FIG. 3. Clusters of "on" pixels in the summed mask are identified as objects and counted as nuclei, as represented in block 86 of FIG. 2 and illustrated in image I of FIG. 3. A watershed split routine is performed on the objects identified in image I to obtain outlines of the objects, as represented in block 88 of FIG. 2. The outlines are then applied to the original image (image A of FIG. 3), as represented in block 90 of FIG. 2 and illustrated in image J of FIG. 3.

The object identification module 57 illustrated in FIG. 2 may be modified to incorporate a routine (prior to block 70) to remove luminescence caused by crystals or other precipitated material in the sample. According to this embodiment, the cells are stained with two different dyes that luminesce at two different, distinguishable colors: a first dye that is a DNA-binding dye, as previously described, and a second dye that does not bind DNA. Dyes suitable for use as the second dye will be apparent to those of skill in the art. As a specific example, the cells may be stained with DAPI and fluorescein isocyanate (FITC).

In this alternative embodiment, the image capture device captures two images. One including luminescence intensity values of the first, DNA-binding dye (e.g., DAPI) and another including luminescence intensity values from the second dye (e.g., FITC). Following optional processing to reduce background luminescence, the second image is then subtracted from the first image. The subtraction removes luminescence caused by crystals or other particulate matter common to both images. The resultant subtracted image is then used as the original image from which LI values are obtained in block 70 of FIG. 2 (and also corresponds to image A of FIG. 3).

The superior ability of the object identification module 57 to identify and define objects as compared with standard object identification modules is illustrated in FIG. 4A. In FIG. 4A, Panel A provides images of DAPI-stained A549 cells that have been treated for 48 hr with dimethylsulfoxide ("DMSO"; 0.2% v/v, vehicle control cells). Panel B provides images of DAPI-stained A549 cells that have been treated for 48 hr with taxol (30 nM). For each Panel, the center image is the image defined by block 70 of FIG. 2. The data were acquired on an ArrayScan II instrument (Cellomics, Inc.). The left-hand images include boundary lines defining objects as identified using the default parameters of the ImagePro® software supplied with the ArrayScan II instrument. The right-hand images include boundary lines defining objects as identified using the embodiment of the object identification module outlined in FIG. 2. For both DMSO and taxol-treated cells, differences between the identification routines, as evidenced by comparing the appropriate corresponding boxed regions in the right- and left-hand images, are clearly visible. When compared to the nuclei that are identified by a skilled worker by visual inspection, which is considered the "gold standard" for identifying nuclei in images such as those presented in FIGS. 3 & 4, the object identification module of the invention is more accurate than conventional object identification routines. This increased accuracy is illustrated in FIG. 4B.

FIG. 4B provides a bar graph illustrating the percentage difference between the number of nuclei identified by a hand-count and the number identified by three different object identification routines: the routine illustrated in FIG. 2; the default routine used by the ImagePro® software supplied with an ArrayScan II instrument (Cellomics, Inc.); and the ImagePro® default modified to include a watershed split routine. In the bar graph of FIG. 4B, positive percentages indicate overcounting and negative percentages indicate undercounting. The optimal value, which corresponds to that obtained by a hand count, is zero. For all cell populations tested (A549 cells treated with DMSO, etoposide, taxol and two test compounds—cmpd 1 and cmpd 2), the ImagePro® default routine greatly under counted the nuclei. On balance, the object identification routine of FIG. 2 provided results most comparable to those obtained with a hand count, demonstrating the increased accuracy of this routine over the other routines tested.

Other methods of identifying objects may be adapted in accordance with the principles taught herein to identify objects with accuracies that approximate those achieved by visual inspection by a skilled worker, and are also within the scope of the invention. For example, any of a number of known adaptive thresholding procedures may be used in conjunction with a watershed split routine to achieve satisfactory results. A specific example of an adaptive thresholding procedure that may be adapted to identify cell nuclei in connection with the principles thought herein is described in U.S. Pat. No. 5,989,835 (see especially Col. 6, line 32 through Col. 7, line 17), which is incorporated herein by reference.

Once objects have been identified, information corresponding to one or more identified nuclei in accordance with the other modules described herein may be obtained based upon the luminescence intensity values of pixels falling within the outlines of the defined nuclei, as represented by block 88 of FIG. 2.

The Cell Proliferation Analysis Module

The cell proliferation analysis module 58 provides information about the ability of cells to divide and proliferate. In general, the cell proliferation analysis module provides such information by counting the number of objects (typically nuclei) identified by the object identification module 57. In one embodiment, the cell proliferation analysis module 57 can be used to screen for and/or identify candidate compounds having anti-proliferative activity. According to this embodiment, the proliferation of cells treated with or exposed to a candidate compound of interest can be monitored with the cell proliferation analysis module 58 of the invention. Comparison of the proliferation activity of the treated cells with control cells (e.g., untreated cells, cells treated with a vehicle or cells treated with a known anti-proliferative compound) provides information about the ability of the candidate compound to inhibit cell proliferation. In a specific embodiment, samples of equal volume are collected from a cell culture as a function of time and analyzed for proliferation with the cell proliferation analysis module 58 of the invention. Cells that do not show increases in the number of counted nuclei as a function of time, or that show lower increases in counted nuclei over time than expected for the particular cell type being assayed are reported as non-proliferating cells. Candidate compounds which induce such effects are reported as having anti-proliferative activity.

In another specific embodiment, adherent cells may be treated with different concentrations of test compound, permitted to incubate for a specified period time and then analyzed with the cell proliferation analysis module 58. Plotting the average number of cells in each sample well as a function of compound concentration provides a curve from which the anti-proliferative $IC_{50}$ (or $EC_{50}$) can be determined. An example of such an assay carried out with the cell proliferation analysis module 58 on taxol-treated A549 cells is provided in FIG. 5. The obtained $EC_{50}$ of 0.0022 µM correlates well with $EC_{50}$s measured by other methods.

The Cell Cycle Analysis Module

The cell cycle analysis module 60 provides information about the cycling or mitotic phase of a cell or population of cells. As a cell divides, its DNA content increases. For cells stained with a DNA-binding luminescent dye, the increase in DNA content leads to an increase in the total luminescence (nuclear brightness) of the identified or defined nucleus. The DNA also begins to aggregate. Thus, the DNA goes from being evenly distributed throughout the entire nucleus to being aggregated at specific locations within the nucleus. For a cell stained with a luminescent DNA-binding dye, owing to this aggregation, the luminescence intensity values corresponding to the nuclei change from having a uniform distribution with a low standard deviation to being highly disperse (i.e., very intense/bright values surrounded by very low/dark values) with a high standard deviation. The cell cycle analysis module 60 calculates total nuclear brightness and standard deviation coordinates corresponding to nuclei identified by the object identification module 57 based upon their respective LI values to provide information about the cycling or mitotic phases of the cells. Specifically, the coordinates provide information about whether a cell is in the G1, S, G2, M1 or M2 phase or, alternatively the percentages of cells within a cell population that are in each of these respective phases.

One embodiment of cell cycle analysis module 60 is represented in FIG. 6A. The first processing step of FIG. 6A is to obtain luminescence intensity values (pixel gray values) corresponding to defined nuclei (block 100); as described above. The gray values of the individual nuclear pixels are summed to provide the total luminescence intensity value (or total nuclear brightness "NB") corresponding to the defined nuclei (block 102). The standard deviation of the luminescence intensities ("SD") of all the pixels within the defined nuclei is also calculated (block 104). A NB versus SD cartesian coordinate is then defined for each cell (or a SD versus NB coordinate) (block 106). The coordinates can be stored in the database 64 for further manipulation, which may include output to a plotting device or a display device. In one embodiment, a coordinate is displayed on an XY plot of NB vs. SD or SD vs. NB that includes boundary lines defining regions of the plot that correspond to particular phases of the cell cycle. The regions may be predefined by the cell cycle analysis module, or they may be determined by the module based upon analysis of similar XY plots of control cells using standard clustering techniques. The regions are correlated to specific phases of the cell cycle based upon their relative positions within the NV vs. SD plot and in accordance with the principles taught below. Alternatively, the boundaries may be drawn by the user based upon visual inspection of an XY plot of control cell or sample cell NB versus SD coordinates. An example of such an XY plot including boundaries defining the five different phases of the cell cycle is provided in FIG. 7.

Alternatively, cell cycle analysis module 60 may include executable computer program code or instructions to filter the coordinate through a predetermined plurality of filters, each of which defines coordinates corresponding to specific phases of the cell cycle (block 108 in FIG. 6A). Such filters can be based upon historical data for cells of a similar type and age as those being assayed, or may be derived from a population of control cells based upon the control cell NB versus SD coordinates using standard clustering techniques. In an alternate embodiment, the filters could be determined and set by the skilled practitioner for the particular cell age and type under study, for example by analysis of histogram plots of samples of control cell or even the test cell populations. If a plurality of cells is analyzed, the cell cycle analysis module 60 may include executable code to determine the percentage of cells of the plurality in each phase of the cell cycle. An example of an embodiment of cell cycle analysis module 60 that calculates percentages of cells in particular phases of the cell cycle is provided in FIG. 6B.

The ability of the cell cycle analysis module 60 to provide information about cell cycling or the mitotic phases of a cell population is illustrated in FIG. 7. FIG. 7 provides a histogram of the coordinates of a population of cells captured by image capture device 30. Cells in the G1 phase, S-phase, G2 phase and two M phases are clearly discernible from the histogram, as indicated by the boundaries. Cells in the resting (G1) phase have a normal (1X) DNA content. In addition, their DNA is uniformly distributed throughout their nuclei. As a consequence, cells in the G1 phase have a very narrow distribution of LI values, and therefore a low SD. Also, since their chromosomes have not begun multiplying, G1 cells will have lower NB values than cells in the S, G2 and M1 phases. On an XY histogram of NB versus SD coordinates, cells in the resting G1 phase are clustered in the lower left-hand region of the graph (see FIG. 7).

As the cells cycle to the synthesis (S) phase, the DNA content of the cells increases, such that S-phase cells have a higher NB than G1-phase cells. As a consequence of their increased DNA content (and hence NB), S-phase cells cluster to the right of G1-phase cells on the histogram.

The DNA content continues to increase uniformly throughout the nucleus and reaches its maximal level as the cells cycle through the G2 phase. Again, since the DNA is fairly uniformly distributed throughout the nucleus, cells in the G2 phase have SD values similar to G1- and S-phase cells. These cells cluster to the right of S-phase cells (see FIG. 7). However, in the initial phases of mitosis (M-phase) the chromosomes segregate and begin dividing. In a stained nucleus, the segregation creates extremely bright spots within the defined nuclei surrounded by a dark background. Thus, cells cycling through the M-phase have high NB values and high SD values compared to cells in the G1-, S- and G2-phases. As indicated in FIG. 7, the coordinates of cells in early M-phase cluster in the upper right-hand corner of the histogram. A significant attribute of the cell cycle analysis module 60 is its ability to distinguish early M-phase cells from late phase M-phase cells.

Owing to the fact that late M-phase cells have divided but still have segregated chromosomes, these cells have a NB similar to G1-phase cells, but have a much higher SD. Thus, these cells can be distinguished from both G1-phase and early M-phase cells with the cell cycle analysis module of the invention, as illustrated in FIG. 7.

The inset of FIG. 7 provides a pie-chart diagram of the percentages of cells in each phase of the cell cycle. The cell population analyzed in FIG. 7 was a population of A549 cells treated with 0.2% (v/v) DMSO for 48 hr, which could serve as a standard for comparison with similar histograms for experimental test cell populations, for example, for comparison with a histogram calculated from a population of identical cells treated with a candidate compound.

As evidenced by FIG. 7, the cell cycle analysis module 60 of the invention can distinguish all five phases or phases of the cell cycle. In contrast, information obtained by FACS cannot distinguish all five phases. In particular, FACS cannot distinguish G2 from M-phase cells. Thus, not only can the cell cycle analysis module of the invention provide information about cell cycling faster and at a lower cost than FACS analyses, the information provided is also of a higher quality and quantity.

Cell cycle data obtained with cell cycle analysis module 60 for candidate test compounds correlates well with data obtained by FACS (data not shown), validating the method as being useful in screening assays. In one embodiment of such a screening assay, the percentages of cells in the various phases of the cell cycle of a population of cells contacted with or exposed to a candidate compound of interest can be compared to known phase distributions for untreated or vehicle treated control cells. Alternatively, a control experiment with a sister culture of synchronous cells can be run simultaneously with the test sample.

An example of cell cycle information obtained with the cell cycle analysis module of the invention for sister cultures of synchronous A549 cells treated with varying concentrations of DMSO, two different compounds known to arrest cells in G2 phase (taxol and etoposide) and two test compounds being assessed for activity, cmpd 1 and cmpd 2, are provided in FIG. 8. For FIG. 8, cells were synchronized with double thymidine treatment. Prior to the last treatment, test compounds were added to the cultures and remained therefor the rest of the experiment. The thymidine was then removed, releasing the cells into the cell cycles. Samples were collected at a designated time point, fixed with aldehyde, stained with DAPI (5 ng/mL) and imaged on an ArrayScan II instrument (Cellomics, Inc.). The digital image data was analyzed using the cell cycle analysis module of the invention. The percentages of cell in the various phases of the cell cycle are indicated in pie-chart format. The concentrations of test compound added are indicated across the bottom of the FIG. 8. All DMSO-treated samples (vehicle control samples) were treated with 0.2% (v/v) DMSO. The various phases of the cell cycle are illustrated on the right-hand most DMSO-treated graph. The numbers above each graph represent the total number of cells analyzed in the particular sample. As clearly visible in FIG. 8, DMSO has no effect on cell cycling. In contrast, both taxol and etoposide arrest the cells in the G2 phase at concentrations as low as 3 μM.

The Cell Death Analysis Module

FIG. 9A illustrates one embodiment of processing steps associated with the operation of the cell death analysis module 62. The first processing step of FIG. 9A is to obtain luminescence intensity (LI) values corresponding to defined nuclei of cells captured by the image capture device (block 130), as described above. Based upon these LI values, the minimum nuclear luminescence intensity values ("MNLI") are obtained (block 132). The MNLI value for a nucleus is the lowest LI value measured for that nucleus, for example, the lowest gray value of the pixels within a specific defined nucleus. At this point, the cell death analysis module 62 may compare the MNLI values of particular cells to a range of predefined MNLI values indicative of viable cells (block 134). A value falling outside this range identifies the cell as being non-viable or dead, whereas a value falling within this range identifies the cell as being viable or alive. Alternatively, the cell death analysis module 62 may be carried out with populations of cells, as illustrated in FIG. 9B. In this instance, MNLI values for a plurality of defined nuclei are obtained (block 142) based upon their LI values (block 140) and the percentage of cells having MNLI values falling outside a specified range of MNLI values is calculated (block 144). This percentage is then compared with a predefined percentage range indicative of a viable cell population (block 146). Cell populations having percentages falling within the predefined range are reported as viable populations, whereas percentages falling outside the predefined range are reported as non-viable populations.

Skilled artisans will recognize that the range of MNLI values indicative of viable cells, as well as the percentages of cells that must fall within this range, will depend upon a variety of factors, which include but are not limited to the type of cell being assayed, the age of the cell being assayed, etc. The range of MNLI values or percentages falling within such ranges that are indicative of viable cells may be determined by the cell death analysis module 62 based upon information (such as cell type, cell age, etc.) input by the user. Alternatively, it may be defined by the user or calculated from a population of control cells (untreated, vehicle-treated or treated with compounds known to induce cell death).

In one embodiment, the range of MNLI values indicative of viable cells may be calculated from control cell MNLI values using standard statistical analyses. For example, the MNLI values that bound a specified percentage or confidence interval, for example, 80%, 90%, 95% or a higher percentage, of the control cell MNLI values may be used as boundaries to defined the range of MNLI values indicative of viable cells. As this range is only exemplary, it will be appreciated that higher or lower percentages may be utilized. As a specified example, the MNLI values that bound 95% of the MNLI values using a standard statistical analysis yields good results. The boundary values may be used in an absolute sense to define a specific LI range (in absolute intensity units). Alternatively, the boundary values may be used in a relative sense to define an interval or spread (e.g., ±X intensity units) of acceptable LI values. When used in a relative sense, the spread or interval may be applied to the statistical mean of MNLI values for a population of test cells to define the range of acceptable MNLI values. Once applied, the percentage of test cells falling within (or without) the range can be calculated to assess whether the cell population is viable or non-viable. A population of test cells is reported as non-viable when the percentage of test cells having MNLI values falling inside the range is less than the confidence percentage or interval used to define the range. For example, if the range of MNLI values indicative of viable cells is defined by the 95% confidence interval of MNLI values of a population of control cells, then a population of test cells is reported as non-viable if less than 95% of its MNLI values fall inside the defined range (or alternatively, when greater than 5% of the test MNLI values fall outside the defined range). Images of individual cells, or of populations of cells, may be inspected visually to confirm that the cells are non-viable.

Another embodiment of a cell death analysis module 62 of the invention is illustrated in FIG. 9C. In this alternative embodiment, an MNLI versus NB coordinate is correlated with each defined cell (block 156) and the percentage of cell coordinates falling outside a range of coordinates indicative of viable cells is calculated (block 158).

Alternatively, the coordinates can be displayed on an XY graph of, e.g., NB versus MNLI, and the viability of the cell population assessed by visual inspection. The graph may include lines bounding a region of coordinates indicative of viable cells. The boundaries may be predetermined information input by the user or based upon experiments performed with control cells of a similar type and age of those being assayed, or they may be obtained from control cells assayed concurrently with the test samples.

The ability of the cell death analysis module 62 to provide information about the ability of a test compound to induce cell death in a cell population is illustrated in FIG. 10. FIG. 10 provides an XY plot of the NB versus MNLI coordinates of control cells treated with DMSO (blue) a control compound that does not induce cell death. The coordinates of these DMSO-treated cells form a tight band of MNLI values. Based on a statistical analysis, 95% of the MNLI values measured from this population fall within a range of 481 to 560 intensity units (i.e., within a range of ±79 intensity units from the statistical mean MNLI value). Visual inspection of images of selected nuclei (shown on the right-hand side of FIG. 10) of this population reveals the cells are viable. The MNLI versus NB coordinates for cells treated with etoposide (magenta), a drug known to arrest mitosis but not induce cell death, also form a tight band. Moreover, 99.5% of the etoposide-treated cells fall within the same band of 481-560 MNLI values. In stark contrast, the coordinates of a cell population treated with Taxol (red), a drug known to induce cell death via apoptosis, do not form a narrow band. For this population, only 83% of the cells are within the 481-560 MNLI value range defined by the DMSO control cell population. Visual inspection of images of etoposide- and taxol-treated cells confirm the viability and non-viability, respectively, of these two treated populations. Also shown in FIG. 10 are data for two test compounds, cmpd 1 (green) and cmpd 2 (yellow). Both MNLI analysis and visual inspection of images of cells treated with these compounds reveals that these two test compounds induced cell death.

The cell-death analysis module of the invention is as accurate as a trained observer, which is considered the "gold standard" in interpreting cell images. The accuracy is illustrated in FIG. 11, which provides a bar graph comparing the percentage of apoptotic cells determined for the cell populations of FIG. 11 using the lowest gray value criteria of the cell-death analysis module of the invention with that determined by visual inspection (hand classification).

The Multiparameter Assay

The invention also provides a high information content multiparameter assay useful for analyzing cellular samples for cell proliferation, cell cycle phase, cell death and/or for screening compounds for anti-cancer utility. In the high information content assay, the object identification module 57 described above is combined with three additional modules: the cell proliferation analysis module 58, the cell cycle analysis module 60 and the cell death analysis module 62. Other embodiments may utilize the modules separately on in any combination. The object identification module 57 identifies and defines nuclei captured by image capture device 30, for example as described in connection with FIGS. 2 and 3, supra and the cell proliferation analysis module 58 counts the identified nuclei. A comparison of the number of captured cell nuclei before and after treatment with a candidate compound of interest provides information about whether the compound inhibits cell proliferation. Alternatively, the number of cells may be counted as a function of time after treatment with the candidate compound to assess whether the treated cells proliferate over time, and hence whether the candidate compound inhibits proliferation. For example, an increase in the number of identified cell nuclei as a function of time is indicative of cell proliferation. No increase over time is indicative of inhibition of proliferation. A decrease in the number of identified nuclei over time is also indicative of inhibition of proliferation and also may be indicative of cell death. As described previously, the cell proliferation analysis module 58 may also be used to measure the $IC_{50}$ or $EC_{50}$ of cell proliferation in screening experiments with varying concentrations of test compound (see, e.g., FIG. 5).

The cell cycle analysis module 60 determines the cell cycle phase of identified cell nuclei captured by image capture device 30, for example as described in connection with FIGS. 6-7, supra. A comparison of the percentage of cells in each phase of the cell cycle before and after treatment with a candidate compound of interest provides information about whether the compound induces changes in the cycling of the cell. As illustrated with FIG. 8B, the cell cycle analysis module 62 can be used to identify compounds that arrest mitosis.

The cell death analysis module 62 determines the MNLI value or MNLI vs. NB coordinate for each identified cell nucleus captured by image capture device 30, for example as described in connection with FIGS. 9 and 10, supra. A comparison of the percentage of MNLI values or coordinates falling within the range of MNLI values or coordinate characteristic of healthy, viable cells before and after treatment with a candidate compound of interest provides information about whether the candidate compound induces cell death.

An advantage of the high information content oncology assay of the invention is its ability to provide information with respect to these multiple parameters (cell proliferation, cell cycling and cell death) simultaneously. Once nuclei are identified using the object identification module 57, LI values corresponding to the identified nuclei are obtained. Information about the various multiple parameters is then provided based upon the measured LI values. Thus, information about numerous parameters important to assessing a candidate compound's usefulness as a potential anticancer agent may be assessed in a single assay.

The multiparameter high information content assay of the invention is extremely flexible and can be carried out in many different formats. For example, information about cell proliferation, cell cycling and cell death may be obtained for a population of control cells (treated or untreated) and compared with similar information obtained from test cells treated or exposed to a candidate compound of interest. Alternatively, the information from the test cells may be compared to known information to assess whether the candidate compound induces changes in the proliferation, cycling or viability of the cells.

The apparatus and high information content assay of the invention were used to analyze cell proliferation, cell death and cell cycling of cells treated with DMSO and compounds known to produce cell cycle arrest (e.g., taxol, etoposide, nocodazole). This information was compared with proliferation and cell cycle information obtained by standard BrDU and FACS assay methods, respectively, on sister cultures of synchronously cycling cells. For the experiment, A549 cells were synchronized with double thymidine treatment: cells were treated with 2 mM thymidine for 18 hr, placed back into normal media for 8 hr followed by a second thymidine treatment for 18 hr. Two hours before the end of this second treatment, test compounds were added to the cultures and remained there for the rest of the experiment. The thymidine was then removed from the cultures, releasing the cells into the cell cycle. Samples were collected at various time points and prepared for analysis. Cells for BrDU assay were ethanol fixed, stained with antibody, incubated with substrate and read immediately on a plate reader (a BrDU kit from Roche Molecular was used according to the packaged instructions). Cells for FACS were prepared according to standard methods. Cells for analysis according to the invention were fixed with aldehyde, stained with DAPI (5 ng/mL) and imaged on an ArrayScan II (Cellomics, Inc.) instrument.

Comparison of data histograms obtained by FACS and the high information content assay of the invention at 0 and 9 hr post-release time points reveals a good correlation between the two methods. However, unlike FACS, the high information content assay of the invention is able to distinguish all five phases of the cell cycle (see, e.g., FIG. 7). Comparison of compound EC50 values obtained with the assay of the invention and those obtained with BrDU also yielded a good correlation.

In sum, these experiments demonstrate that information about cell proliferation, cell death and cell cycling can be obtained with a single high information content assay according to the invention. The high information content assay acquired this information up to five times faster than comparable assays and at a significant cost savings over the other methods (approx. $50/plate savings). The assay has been used to provide information about cell proliferation, cell death and cell cycling in the context of screening experiments, permitting large numbers of candidate compounds to be quickly, reliably and accurately screened to assess the candidate compounds for anti-cancer activity. Quite significantly, with the multiparameter high information content assay of the invention, information as to whether a candidate compound is cytotoxic or cytostatic, which cannot be obtained from conventional single-parameter assays, can be obtained in a single assay. The assay is also able to distinguish cells in all five phases of the cell cycle. In particular, the G2 and M phases can be readily distinguishable. Thus, the assay of the invention provides cell cycle information that cannot be obtained with conventional single parameter, FACS or conventional multiparameter assays.

The invention having been described, it will be apparent to ordinarily skilled artisans that numerous changes and modifications can be made thereto without departing from the spirit or the scope of the appended claims. As a specific example, skilled artisans will understand that while the high information content assay has been exemplified in the context of four modules, once nuclei are identified, the cell proliferation, cell cycle and cell death modules may be used alone or in one or more different combinations.

All publications and patents cited herein are incorporated by reference for all purposes.

What is claimed is:

1. A method of determining the cell cycle phase of a cell, comprising the steps of:
    staining the nucleus of a cell with a luminescent DNA-binding reporter molecule;
    imaging the nucleus of said cell to obtain nuclear luminescence intensity (NLI) values;
    determining a cell cycle phase by:
        i) comparing total nuclear brightness versus standard deviation of nuclear brightness using the NLI values to obtain a cell coordinate; and
        ii) filtering the cell coordinate through a plurality of filters, each of which defines a set of total nuclear brightness versus standard deviation of nuclear brightness coordinates indicative of a particular phase of the cell cycle; and
    displaying the phase of cell cycle of the cell,
    wherein the determining and displaying is done by a computer programmed to carry out the determining and displaying.

2. The method of claim 1, in which said LI values corresponding to the nucleus of the cell are identified by,
    obtaining LI values from said sample to yield a first set of digital intensity data;
    defining as preliminary objects groups of at least 50 LI values that are above a first threshold value and defining boundaries around said preliminary objects;
    defining a first digital mask based upon the preliminary objects, said first digital mask assigning a binomial value of "1" to LI values within the defined boundaries and a binomial value of "0" to all other LI values;
    dilating the first digital mask;
    subtracting the dilated digital mask from the first set of digital intensity data to yield a subtracted set of digital intensity data;
    defining as remainder objects within the subtracted set of digital intensity data groups of at least 20 LI values that are above a second threshold value and have a roundness value suitable for a morphology of said cell, and defining boundaries around said remainder objects;
    defining a digital remainder mask based upon the remainder objects, said digital remainder mask assigning a binomial value of "1" to subtracted LI values within the remainder object boundaries and a binomial value of "0" to all other subtracted LI values;

adding the first digital mask and the remainder digital mask to obtain a resultant summed mask;

performing a watershed split routine to the summed mask and defining boundaries around the resultant objects; and applying the boundaries of the resultant objects to the first set of digital intensity data.

3. The method of claim 2, wherein said first and second threshold values are equivalent.

4. The method of claim 2, wherein said dilating the first digital mask is for two passes using a 3×3 cross filter.

5. The method of claim 1 in which the filtering is carried out by displaying the cell coordinate on a graph of total nuclear brightness versus standard deviation of nuclear brightness which includes boundaries defining regions of total nuclear brightness versus standard deviation of nuclear brightness coordinates corresponding to particular phases of the cell cycle and determining in which region the cell coordinate resides.

6. The method of claim 1 in which the cell is treated with a candidate compound for inducing a change in the cycling of the cell.

7. The method of claim 6 in which the filtering is carried out by displaying the cell ordinates on an XY graph of total nuclear brightness versus standard deviation of nuclear brightness which includes boundaries defining regions of total nuclear brightness versus standard deviation of nuclear brightness coordinates corresponding to particular phases of the cell cycle and determining in which region the cell coordinates reside.

8. The method of claim 6, in which the cell cycle phase of the cell is compared to the cell cycle phase of a control cell that is not treated with said candidate compound.

9. The method of claim 1, in which the luminescence intensity values are collected by an image capture device, wherein said device is connected to a computer, said computer including a peripheral interface circuit to receive said luminescence intensity values, a central processing unit connected to said peripheral interface circuit, and a memory connected to said central processing unit, said memory operating under the control of said central processing unit, said memory including a cell cycle analysis module to calculate the total nuclear brightness versus standard deviation of nuclear brightness coordinate.

10. The method of claim 1 in which the luminescent DNA-binding reporter molecule is a fluorescent DNA-binding dye.

11. A method of determining whether a candidate compound induces a change in the cycling of a cell, comprising the steps of:

contacting a plurality of cells with the candidate compound;

staining the nuclei of the plurality of cells with a luminescent DNA-binding reporter molecule;

imaging the nuclei of the plurality of cells to obtain nuclear luminescence intensity (NLI) values;

determining a cell cycle phase for each cell of said plurality of cells by:

i) comparing total nuclear brightness versus standard deviation of nuclear brightness using the NLI values to obtain a cell coordinate; and ii) filtering the cell coordinate through a plurality of filters, each of which defines a set of total nuclear brightness versus standard deviation of nuclear brightness coordinates indicative of a particular phase of the cell cycle;

wherein the determining is done by a computer programmed to carry out said determining;

comparing the cell cycle phase of the plurality of cells to the cell cycle phase of control cells; and displaying whether the compound induces a change in the cycling of the cells.

12. A physical computer readable storage medium to direct a computer to function in a specified manner, comprising:

executable instructions to calculate treated cell total nuclear brightness versus standard deviation of nuclear brightness coordinates based upon nuclear luminescence values corresponding to nuclei of cells treated with a candidate compound of interest, said treated cells being stained with a luminescent DNA-binding reporter molecule;

executable instructions to assess the percentage of treated cell coordinates falling within sets of defined total nuclear brightness versus standard deviation of nuclear brightness coordinates indicative of particular phases of the cell cycle, thereby determining the percentage of treated cells within each defined phase of the cell cycle; and executable instructions to display the percentage of treated cells within each defined phase of the cell cycle.

13. The computer memory of claim 12 further including executable instructions for comparing the percentages for the treated cells with percentages derived from control cells.

14. A physical computer readable storage medium to direct a computer to function in a specified manner, comprising:

executable instructions to calculate treated cell total nuclear brightness versus standard deviation of nuclear brightness coordinates based upon nuclear luminescence values corresponding to nuclei of cells treated with a candidate compound of interest, said treated cells being stained with a luminescent DNA-binding reporter molecule; and executable instructions for displaying said treated cell coordinates on an XY graph of total nuclear brightness versus standard deviation of nuclear brightness which includes boundaries defining regions on the XY graph corresponding to defined phases of the cell cycle.

15. The computer memory of claim 14, further including executable instructions for calculating the percentage of treated cell coordinates residing within each region, thereby determining the percentage of treated cells in each defined phase of the cell cycle.

16. A physical computer readable storage medium to direct a computer to function in a specified manner, comprising:

executable instructions to calculate treated cell total nuclear brightness versus standard deviation of nuclear brightness coordinates based upon nuclear luminescence values corresponding to nuclei of cells treated with a candidate compound of interest, said treated cells being stained with a luminescent DNA-binding reporter molecule;

executable instructions to define sets of total nuclear brightness versus standard deviation of nuclear brightness coordinates corresponding to particular phases of the cell cycle, said sets being based upon the distribution of treated cell coordinates;

executable instructions to assess the percentage of treated cell coordinates falling within each defined set of coordinates, thereby determining the percentage of treated cells within each defined phase of the cell cycle, and executable instructions to display the percentage of treated cells within each defined phase of the cell cycle.

17. A computer program product for use in conjunction with a computer system, the computer program product comprising a physical computer readable storage medium and a computer program mechanism embedded therein, the computer program mechanism, comprising: a program module that directs the computer to function in a specified manner, the program module including instructions for:

calculating treated cell total nuclear brightness versus standard deviation of nuclear brightness coordinates based upon nuclear luminescence values corresponding to nuclei of cells treated with a candidate compound of interest, said treated cells being stained with a luminescent DNA-binding reporter molecule;

defining sets of total nuclear brightness versus standard deviation of nuclear brightness coordinates corresponding to particular phases of the cell cycle, said sets being based upon the distribution of treated cell coordinates;

assessing the percentage of treated cell coordinates falling within each defined set of coordinates, thereby determining the percentage of treated cells within each defined phase of the cell cycle, and displaying the percentage of treated cells within each defined phase of the cell cycle.

* * * * *